US 6,737,276 B1

(12) United States Patent
Voss et al.

(10) Patent No.: US 6,737,276 B1
(45) Date of Patent: May 18, 2004

(54) METHOD AND DEVICE FOR DETERMINING THE TOTAL ORGANIC CARBON CONTENT IN LIQUIDS, ESPECIALLY ULTRA-PURE WATER

(75) Inventors: Werner Voss, Hamburg (DE); Erich Messerschmitt, Niedernhausen (DE); Herbert Bendlin, Ransbach-Baumbach (DE)

(73) Assignee: Maihak Aktiengesellschaft, Hamburg (DE)

( * ) Notice: Subject to any disclaimer, the term of this patent is extended or adjusted under 35 U.S.C. 154(b) by 0 days.

(21) Appl. No.: 09/622,597
(22) PCT Filed: Feb. 17, 1999
(86) PCT No.: PCT/EP99/01024
§ 371 (c)(1), (2), (4) Date: Aug. 21, 2000
(87) PCT Pub. No.: WO99/42824
PCT Pub. Date: Aug. 26, 1999

(30) Foreign Application Priority Data

Feb. 19, 1998 (DE) .......................... 198 06 854

(51) Int. Cl.$^7$ .................... G01N 33/00; G01N 27/00
(52) U.S. Cl. .................. 436/146; 422/58; 422/68.1; 422/78; 422/80; 422/102; 422/103; 422/145
(58) Field of Search ............................ 436/146; 422/58, 422/68.1, 78, 80, 102, 103, 145

(56) References Cited

U.S. PATENT DOCUMENTS

| 4,868,127 A | * | 9/1989 | Blades et al. | .......... 422/186.04 |
|---|---|---|---|---|
| 5,132,094 A | * | 7/1992 | Godec et al. | ............... 422/68.1 |
| 5,275,957 A | * | 1/1994 | Blades et al. | ............. 422/186.3 |
| 5,798,271 A | * | 8/1998 | Godec et al. | .................. 422/78 |
| 5,902,751 A | * | 5/1999 | Godec et al. | .................. 422/78 |
| 6,007,777 A | * | 12/1999 | Purcell et al. | ................. 422/80 |
| 6,444,474 B1 | * | 9/2002 | Thomas et al. | ................ 422/58 |

FOREIGN PATENT DOCUMENTS

| DE | 195 00 803 A1 | 12/1995 |
|---|---|---|
| JP | 07055798 A | 3/1995 |

OTHER PUBLICATIONS

Uwe Jessen, "Uberachung des Kohlenstoffgehalts in Wasser/Dampf–Kreislaufen der Stromerzeugung", *WLB Wasser Luft und Boden*, Issue No. 4 of 1997, pp. 32–35.

* cited by examiner

Primary Examiner—Arlen Soderquist
Assistant Examiner—Monique T. Cole
(74) Attorney, Agent, or Firm—Stites & Harbison PLLC; B. Aaron Schulman

(57) ABSTRACT

A method and an apparatus is provided for the determination of the content of organic carbon (TOC) of liquids, in particular ultra-pure water, wherein a liquid sample under investigation is located in a reaction chamber and carbon present in the liquid is statically oxidized to mainly carbon dioxide. After oxidation of the carbon, the sample quantity is transferred to a measuring cell, connected to the reaction chamber by liquid entering the reaction chamber from the outside the reaction chamber, where (i.e. in the measuring cell) the carbon concentration of the sample, which is proportional to the carbon content, is dynamically registered as the sample flows through the measuring cell.

31 Claims, 3 Drawing Sheets

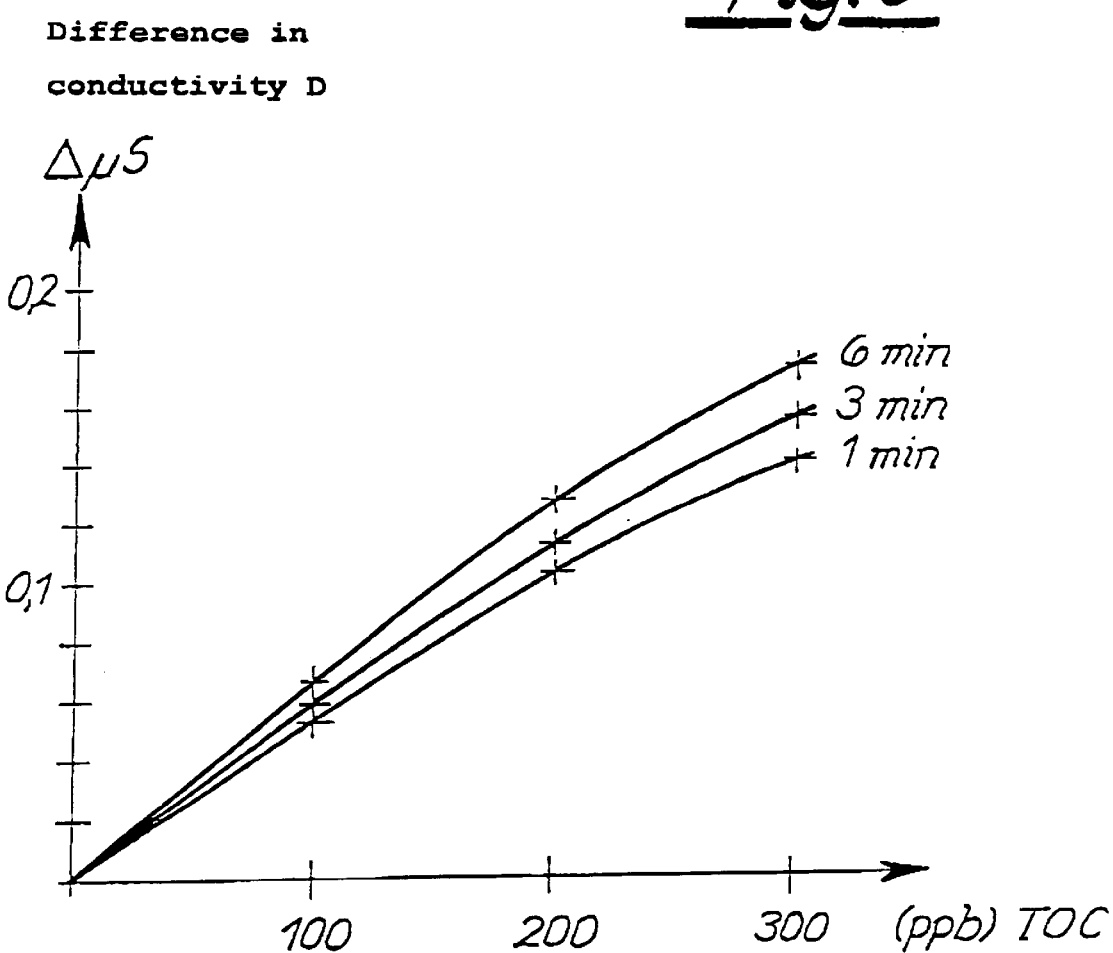

METHOD AND DEVICE FOR DETERMINING THE TOTAL ORGANIC CARBON CONTENT IN LIQUIDS, ESPECIALLY ULTRA-PURE WATER

The invention concerns a procedure for the determination of the total organic carbon (TOC) content of liquids, in particular that of ultra-pure water, whereby a sample of the liquid under investigation is directed into a reaction chamber and is treated statically batch by batch by the use of UV radiation, for oxidising carbon mainly to carbon dioxide, the sample quantity is then transferred by liquid entering the reaction chamber from the outside to a measuring cell connected to the reaction chamber, where the conductivity is measured and then the carbon content (TOC) is found from the conductivity measurements.

The TOC content of a liquid is the total content of organic carbon. The determination of this carbon content, in particular in ultra-pure water, is of special importance to modern high technologies. At this point, ultra-pure water which is necessary for semiconductor production is intended. However, the pharmaceutical industry also depends upon the reliable monitoring of traces of organic contamination. Even the slightest contamination with hydrocarbon compounds, aliphatics and/or aromatic alcohols etc. is to be avoided at all costs. In the past, methods of measurement and their attendant apparatus have been developed, which were able to determine the content of organic carbon in ultra-pure water over a wide range, from a few ppm (parts per million; $10^{-6}$) to a few ppb (parts per billion; $10^{-9}$).

U.S. Pat. No. 3,958,941 describes a procedure whereby with the aid of a dual circuit system the organic components are oxidised in a reaction chamber by irradiation with UV light. The carbon dioxide produced by this procedure is transferred to a measuring cell filled with ultra-pure water, via a separate (air-) duct. The conductivity of the contents of the measuring cell is determined, which increases due to the reaction with the introduction of carbon dioxide.

A method such as this requires the execution of various measurements in advance, in order to calibrate the measuring cell, or the conductivity measuring apparatus used. Apart from that, the accuracy when only a small amount of organic carbon compounds is present is low, as measuring errors caused by the UV radiation cannot be ruled out. Moreover, it is mandatory that the carbon dioxide developed in the reaction chamber be transferred to the measuring cell and dissolved in the ultra-pure water. This type of procedure is not just complicated, but also leads to undesirable sources of error, for example the solubility of the carbon dioxide in the measuring cell changes, depending upon temperature. Apart from this, atmospheric carbon dioxide which unintentionally finds its way into the apparatus, can interfere with the accuracy of measurement.

An attempt at overcoming the above-mentioned drawbacks is made in the European script 0 150 923. The carbon content of a static water sample is determined in such a way that this water sample is placed in a chamber with conductivity sensors and statically held there. A UV lamp, which is mounted on the outside of the chamber, irradiates the water sample until the carbon compounds are completely oxidised. The difference in the conductivities measured before and after UV irradiation should then represent the equivalent of the TOC content. The system described in EP 0 150 923 is completely closed and together with its static measurements, may well prevent the influence of contamination and the introduction of carbon dioxide from the atmosphere.

However, the price paid for this is the disadvantage that the UV lamp which is mounted outside of the chamber or measuring cell, has a relatively small angle of illumination, and can deliver very little effective radiation into the measuring cell or oxidation chamber. In addition, a quartz window is fitted as the optically transparent closure of the measuring cell, which corresponds to radiation losses due to absorption and reflection. These losses are in addition to the unavoidable losses caused by the quartz glass envelope of the UV lamp.

Moreover, due to the measuring electrodes which are mounted inside the oxidation chamber or measuring cell, it is necessary that a thick stratum of water awaiting irradiation be present, which exceeds the effective penetration of the UV radiation. Consequently, the organic contents of the static water in the chamber are oxidised only very incompletely and slowly. Although TOC concentrations in the order of ppb can be determined using this apparatus, this leads to undesirably high measuring errors, especially in the lowest measuring range. In fact, oxidation times of up to approx. 10 minutes are necessary, which produce conductivity values which asymptotically approach a limit which has to be mathematically determined. In any case, the conductivity measurement can only be taken while the UV lamp is switched on, which—as in the case of U.S. Pat. No. 3,958,941—creates considerable interference in the measuring electronics, which have to be present, as UV lamps are usually driven by a high voltage in the order of several hundred volts.

A further disadvantage of EP 0 150 923 is that, due to the relatively large quantity of water contained in the measuring cell or oxidation chamber, the measurement of conductivity reacts slowly, thus displaying a large time constant. Also, due to the design of this apparatus, areas of shadow can form behind the measuring electrodes, which will not be reached by the UV radiation. In addition, the UV lamp will operate at high temperatures the longer it is in use, making not just a heat sink necessary, but also possibly leading to undesirable measuring errors, due to overheating, as the conductivity determined is not just a function of the carbon dioxide concentration in the water, but also of temperature. Consequently it is important to maintain the liquid or water in the measuring cell at as constant a temperature as possible, which is not possible in the case of the present scheme due to the peculiarities of the design, making a rapid temperature measurement, and possibly temperature compensation necessary. In addition, a further (indirect) effect comes into play, which can be explained by the fact that the intensity of illumination of a mercury vapour lamp, regularly used to produce the UV radiation, decreases with rising temperature. In any case, considerable problems are caused by the long oxidation times, which need to be avoided at all costs, in order to increase the accuracy of the measurements.

Above and beyond this, it is known from the German publication 32 23 167 that water can be continuously examined for decomposable organic and/or inorganic carbon compounds. To this purpose, the water under investigation is continuously passed through an irradiation cell, where here the pH value is set to between 7.0 and 7.3. There is a subsequent irradiation of the water under investigation with UV light, and a continuous transfer of the gas mixture which contains the volatile products of decomposition from the irradiation cell to a measuring cell. The above-mentioned volatile products of decomposition are continuously partially extracted from the water under investigation by means of a circulation gas. Then the IR (infrared) absorption of the circulation gas is measured and/or the circulation gas is transferred to a conductivity cell which supports a continuous stream, and partially dissolved there, whereby the conductivity of the water changes. The inorganic carbon compounds which are normally broken down by acids, do not need to be first removed, in order to determine the presence of organic carbon compounds. The procedure for the determination of the organic carbon content is practically the same as described in U.S. Pat. No. 3,958,941, mentioned above, and result in the same disadvantages as described before.

Finally, an apparatus for the production of ultra-pure water is known from the U.S. Pat. No. 5,272,091 which consists of an oxidation chamber set in the main stream, in which the entire quantity of water to be purified is treated with UV radiation as it passes through. Simultaneously, a base value for conductivity is taken upstream of the oxidation chamber in a measuring cell, while downstream of the oxidation chamber in a further measuring cell, a higher value, due to the irradiation is measured. The difference between this and the base value is an indication of the content of organic carbon destroyed by the UV irradiation. Since the values for conductivity can vary with the type of carbon compounds and due to other factors, from time to time the production of ultra-pure water is interrupted and sequentially, batch by batch, several amounts, being the contents of the oxidation chamber, are exposed for various lengths of time to UV radiation. After each irradiation, the main stream of water is temporarily pumped through the oxidation chamber again and a measurement is taken in the downstream measuring cell, and correlated with the length of time of the irradiation. From this set of results, a reference value for the for the rise in conductivity when the entire organic carbon content is destroyed can be calculated, which can then be compared with the rise in conductivity calculated from the measurements taken upstream and downstream of the oxidation chamber during the subsequent treatment of continually flowing water.

This last known procedure suffers from the disadvantage of great inaccuracy, compared to measuring procedures with reaction chambers and measuring cells which are not deployed in the main stream of a system for the treatment of water and need therefore only to take sample quantities, since in the main stream all flow cross-sections have to be large and it would take a very long time if the entire organic carbon were to be destroyed by UV radiation in the large volume of water in the oxidation chamber. The aforementioned problem, that the UV radiation is only effective down to a small depth of water, arises here in an extreme form. This is why, in the case of this known apparatus, the duration of the irradiation is relatively short, in principle the total oxidation of the organic carbon is foregone, instead of which the conductivity reference value is determined by extrapolation, which introduces a further source of inaccuracy. Finally, the accuracy of the measurement procedure in the measuring cell is affected, since its cross-sections are also adapted to the rate of flow of the main stream. Moreover, only a single conductivity value is determined for each batch measured, and not, as the irradiated volume of water is pushed out of the oxidation chamber, a conductivity profile which can be analysed, of the column of water flowing out. The last point will fail, due to the fact that the water, which has undergone irradiation of varying intensity, is mixed within the large flow cross-sections on its way to the measuring cell, so that complete destruction of the organic carbon content, represented by a peak will not occur.

It is the object of the invention to develop the last described procedure so that the carbon content of the liquid under investigation can be determined—also in the ppb range—employing a simple construction and high oxidation effect, quickly and reliably with few measuring errors. A specially designed apparatus shall also be created.

In order to achieve this object, the invention suggests that in a procedure of the above mentioned sort, the sample quantity after carbon oxidation with a UV immersion lamp be transferred to a conductivity measuring cell which is connected to the reaction chamber, yet is separate from the reaction chamber, by liquid entering the reaction chamber from the outside, and that here the carbon concentration which is proportional to the carbon content of the liquid be dynamically registered as it flows through the measuring cell. A usual procedure is to clean the reaction chamber and the measuring cell by flushing liquid through them—of course without external energy—before and/or after determination of the carbon concentration. This flushing liquid is usually the liquid under investigation, which is also generally used as the liquid which enters the reaction chamber from the outside after oxidation of the carbon. In any case, defined values for the carbon concentration in the liquid under investigation can be given, before carbon oxidation and/or after the carbon concentration is determined. This should be as small as possible. In the case of this invention, the carbon dioxide concentration in the liquid is determined by means of conductivity measurements. The invention rests upon the concept that dissolved carbon dioxide in a liquid, usually water, reduces the resistance due to the forming of hydrogen ions and carbonate ions, so that the conductivity rises.

The result is that in any case, conductivity measurements can be given, which for the purposes of the invention will be designated as the base value, corresponding to the carbon dioxide concentration in the untreated liquid. This base value is measured as well as the maximum value attained for the carbon dioxide concentration as the liquid enriched with carbon dioxide flows through the measuring cell. Thereafter, the difference between the maximum value and base value, which is proportional to the carbon content of the liquid, is regularly calculated (taking non-linearities in the aforementioned relationship into account).

In summary, the invention uses the fact that the untreated liquid corresponds to a base value of conductivity, which approaches the maximum value for conductivity or carbon dioxide concentration as soon as the volume of liquid which has been treated in the reaction chamber before, leaves the measuring cell due to flow through the system. One can consider the volume of liquid of the sample, which has statically been brought to the oxidation of the carbon with external energy, to be a column of liquid which is "pushed" downstream into the connected measuring cell by the liquid entering the reaction chamber from the outside. This treated column of liquid now flows through the measuring cell, where the carbon dioxide concentration, which is proportional to the carbon content—in this case the conductivity—is dynamically determined. The accompanying measured signal of conductivity increases and subsequently decreases over time, forming a peak, the maximum of which can be determined without difficulty. This is usually done in that the measured signal is tracked over time in a control/analysis unit, connected to the conductivity sensor, that is to say the gradient is determined by differentiation over time. The maximum value of conductivity is arrived at when this gradient reaches a value of zero. This maximum value of conductivity can be set in relation to the base value of conductivity or carbon dioxide concentration by taking the difference. This difference indicates the carbon dioxide concentration, produced by oxidation, of the liquid under investigation. From this carbon dioxide concentration, the carbon content of the liquid under investigation can be determined without difficulty. Yet attention is directed to the exemplary EP 0 150 923 and the article quoted therein, "A New Approach to the Measurement of Organic Carbon" by Poirier et al. (American Laboratory, December 1978).

The external energy for the oxidation of the carbon in the liquid under investigation is supplied by a UV lamp which is immersed in the liquid under investigation in the reaction chamber. This UV lamp can be a mercury vapour lamp. Normally this type of source of radiation emits in a wavelength range of between 10 and 380 nm, predominantly between 170 and 260 nm.

First of all, a simple design, according to these inventive measures achieves a high oxidation effect. This is simply explained by the fact that in the preferred configuration, a UV immersion lamp is immersed in the reaction chamber and is in direct contact with the liquid under investigation in the reaction chamber. In this connection, work can be done on small sample quantities leading to small cross-sectional dimensions in the reaction chamber, so that in any case, the cross-sectional dimension can be matched to the depth of penetration of the UV lamp. Apart from this, due to the direct coupling of the UV lamp into the reaction chamber, absorption and reflection losses resulting from a quartz closing window are minimised. This method has the further benefit that auxiliary cooling of the UV lamp is unnecessary, since short oxidation times are attainable, due to the small depth of penetration and high intensity of irradiation. Moreover, the cleaning phases of liquid flushing which precede and follow ensure a stable temperature condition for the UV lamp.

Further, a quick and reliable determination of the carbon dioxide concentration from the conductivity measurements is possible, since this relies only on the determination of the base value and maximum value of the carbon dioxide concentration or conductivity. A measurement of this nature can be done quickly, without any trouble and without serious measuring errors, since background effects have, so to speak, been eliminated. Furthermore, the constancy of temperature of the UV immersion lamp results in a further reduction in measuring errors, since neither a reduction in the intensity of radiation due to temperature, nor a warming of the liquid treated in the reaction chamber is to be expected. It follows that the effects of temperature when measuring conductivity can be ruled out. Finally, it should be taken into account that since the measurements are taken when the UV lamp is switched off, interference in the conductivity sensor, or sensors, as well as in the control/analysis unit is reliably prevented. In addition, the technical properties of the measuring cell can be optimised and no account need be taken of a good transparency to UV radiation. Since the UV lamp is in constant contact with the water or liquid to be gauged, no additional heat dissipation via cooling fins is necessary, so that not only the temperature constancy is improved, but also cost improvements can be asserted. The UV lamp works constantly at its optimal operating temperature, i.e. in the temperature range with the maximum intensity of radiation. Finally, it should not go unmentioned that the UV lamp can be exchanged very easily, since as already stated, it is an immersion UV lamp which is mounted in a reaction chamber which in general is of simple design and independent of the measuring cell. These are the main advantages of the invention.

The subject of the invention is also an apparatus for the determination of the organic carbon (TOC) content of liquids according to claim 5. Advantageous designs of this apparatus are described in claims 6 to 14.

The following explains the invention in more detail, with the aid of a drawing showing just one version as an example.

FIG. 3 depicts the determined differences in conductivity, dependent upon oxidation time and differing TOC concentrations.

Figure 1:
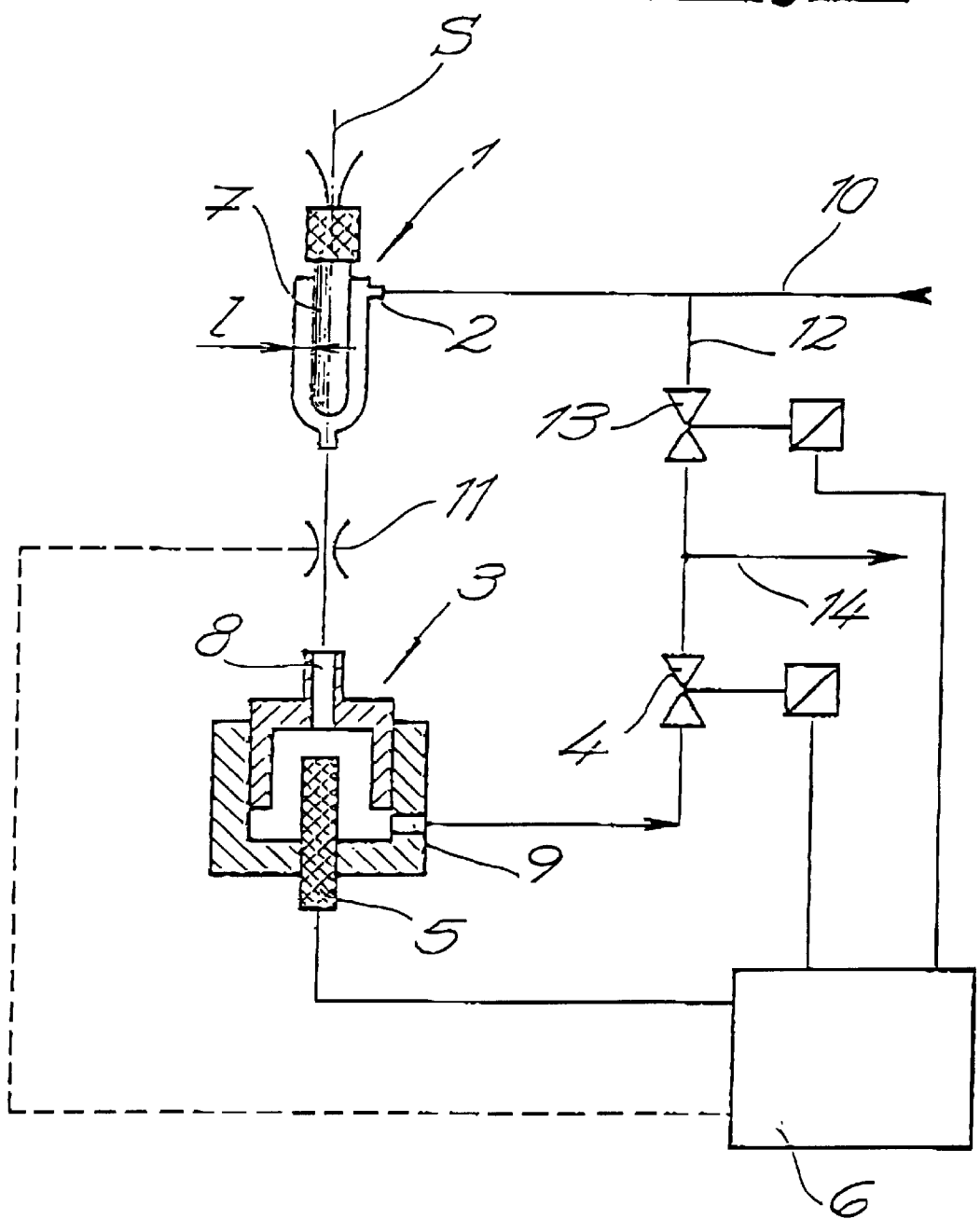
FIG. 1 shows a schematic drawing of the apparatus according to the invention.

The figures show an apparatus for the determination of organic carbon content (TOC) in liquids, in the case of this example, in ultra-pure water. In its basic configuration, this apparatus exhibits a reaction chamber 1 with inlet 2 for the accommodation of a sample quantity of the liquid under investigation and the static oxidisation of the carbon dissolved therein. In addition, a measuring cell 3 is connected to the reaction chamber 1, yet is separate from the reaction chamber 1. On the output side of the measuring cell 3 there is a cut-off device 4, in this example an electro-magnetically controlled valve 4. This valve 4, or the cut-off device 4 can be closed after the introduction of a sample quantity of the liquid under investigation into the reaction chamber 1 and can be opened after static oxidation of the carbon dissolved in the liquid to carbon dioxide in the reaction chamber 1. The carbon dioxide concentration, proportional to the carbon content of the liquid can be dynamically registered as it flows through the measuring cell 3. To this purpose, in this example a conductivity sensor 5 is fitted to the measuring cell 3. This conductivity sensor 5 is connected to a control/analysis unit 6. The sample quantity is transferred to the connected measuring cell 3 after oxidation in the reaction chamber 1 and after the opening of valve 4 by liquid which enters the reaction chamber 1 from the outside.

External energy is used to oxidise the carbon by means of a UV lamp 7. It is designed as a UV immersion lamp 7 and together with the reaction chamber 1 forms a compact assembly unit. The UV immersion lamp 7 is mounted in the middle, on an axis of symmetry S, where the reaction chamber 1 and the immersion lamp 7 are rotationally symmetrically formed with regard to the axis of symmetry S. The measuring cell 3, as seen in FIG. 1 is also formed (rotationally) symmetrically and has an inlet 8 and an outlet 9, both of the same cross-sectional size. The oxidised liquid under investigation therefore flows with constant velocity through the measuring cell 3 with inlet 8 and outlet 9.

The reaction chamber 1 is rotationally symmetrically formed and exhibits the shape of a rotating U-pipe, mainly with a cross-sectional dimension 1 of between 1 and 5 mm. This cross-sectional dimension 1 is matched to the depth of penetration of the UV lamp 7 into the water to be oxidised or the water under investigation or the liquid. This, i.e. the liquid or sample quantity is fed into the reaction chamber 1 via a supply pipe 10 and inlet 2.

In order to regulate the rate of flow through the measuring cell 3, an adjustable choke valve 11 is fitted between reaction chamber 1 and measuring cell 3. Finally, there is a bypass circuit 12 parallel to reaction chamber 1 and measuring cell 3 with a controlled valve 13. In this example, the valve 13, as in the case of the cut-off device 4, is an electro-magnetically controlled valve 13. All of the valves 4, 13 together with the conductivity sensor 5 are connected to the control/analysis unit 6. In an alternative version, the adjustable choke valve 11 can also be connected to the control/analysis unit 6, so that the rate of flow through the measuring cell 3 can be set on this unit, which alters the cross-sectional area of the choke valve 11.

The following explains the operation of the apparatus described above. The liquid under investigation or the ultra-pure water as in this example, is examined for its content of carbon (TOC) by directing a sample quantity of the liquid into the reaction chamber 1 and separate from the liquid itself (i.e. with valve 4 closed) is statically brought to oxidation, carbon into mainly carbon dioxide, by means of UV radiation from the UV immersion lamp 7. Before a sample quantity is introduced into the reaction chamber 1, reaction chamber 1 and measuring cell 3 are cleaned by means of liquid flowing through them. A similar cleaning step can also take place after determination of the carbon dioxide concentration. In any case, the UV immersion lamp 7 is switched off during this period.

In particular, water reaches the reaction chamber 1 via the supply pipe 10 and the inlet 2 and goes from there via the choke valve 11 to the measuring cell 3, to leave in the direction of the arrow, via outlet 9 and valve 4. During this cleaning phase valve 13 is closed. The pressure necessary to ensure flow, is delivered by that usually present in an ultra-pure water system. After the valves 4 and 13 close, the UV immersion lamp 7 is switched on and oxidation of the organic contents of the sample quantity confined in reaction chamber 1 takes place, under static conditions. When oxidation is complete, the UV lamp 7 is turned off and both solenoids 4 and 13 are opened. This results in a portion of the water flowing in via supply line 10 making its way via bypass 12 and valve 13 to outlet 14. A small quantity of the incoming water flows via the choke valve 11 through the measuring cell 3. In particular, this water or liquid entering the reaction chamber 1 from the outside ensures that the (oxidised) sample quantity is transferred from the reaction chamber 1 to the connected measuring cell 3 via the choke valve 11. The registration of the carbon dioxide concentration, which is proportional to the carbon content then takes place while passing through measuring cell 3, i.e. dynamically. After this, the sample quantity makes its way via the drain 9 and valve 4 to the outlet line 14.

Figure 2:
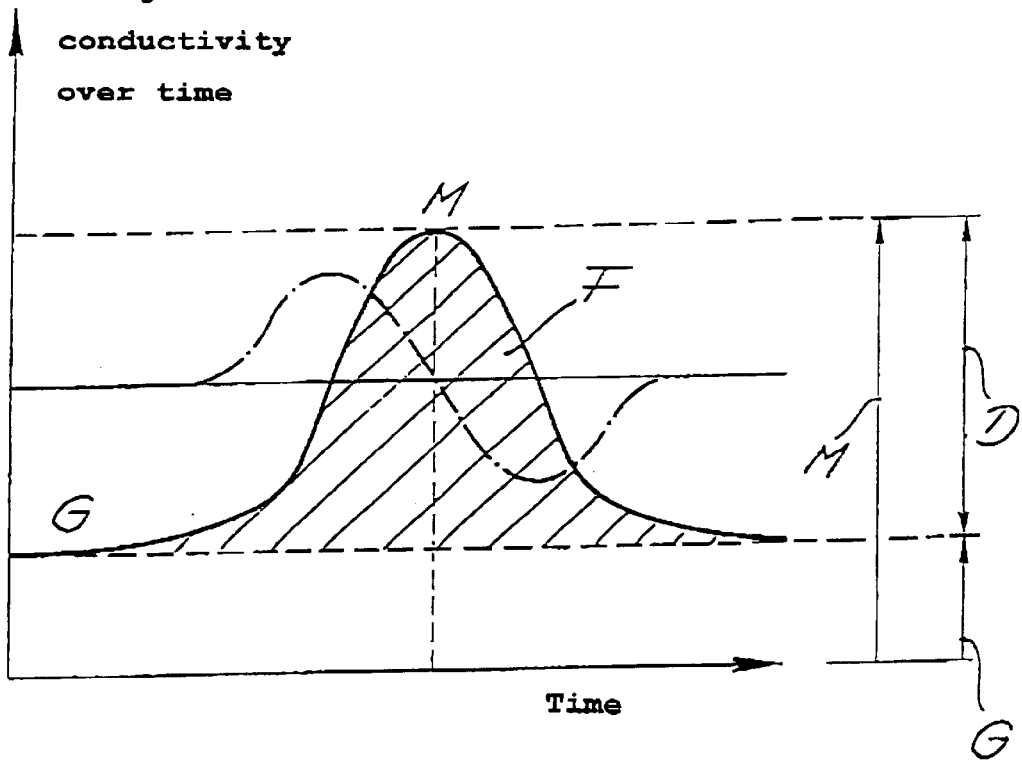
FIG. 2 shows the time-dependent conductivity signal, measured in the measuring cell.

The conductivity sensor 5 delivers a conductivity signal as the sample quantity flows through, as schematically illustrated in FIG. 2. That is, during the course of the liquid or sample quantity enriched with carbon dioxide flowing through, a maximum value of the carbon dioxide concentration or conductivity M occurs (see the solid line in FIG. 2), relative to the base value G, which corresponds to untreated liquid or water. This maximum value M can easily be determined with the aid of the control/analysis unit 6 by differentiation over time of the conductivity signal. This differentiated conductivity signal over time is illustrated in FIG. 2 schematically by the dashed/dotted line. The maximum value M corresponds to the zero intercept of this "derivative signal". From the maximum value M and the base value G, the difference, $$D = M - G \quad (1.1)$$

proportional to the carbon content of the liquid can be found, taking non-linearities into account. This difference D is an indication of the carbon content (TOC) as already explained. Indeed, a largely linear relationship exists between D and TOC with known (non-linear) deviations (see FIG. 3). More accurate methods of calculation use the area F, shown cross-hatched in FIG. 2 for the determination of the TOC value, instead of the calculated value D, according to equation 1.1. The area F represents the integral of the conductivity signal, reduced by the base value G. In this case F=D, as it were. Differences in conductivity D are plotted against their corresponding carbon concentrations TOC in FIG. 3.

The very small cross-sectional dimension 1 in the reaction chamber 1 and the direct contact of the liquid or water with the UV immersion lamp here leads to a short oxidation time, since absorption and reflection losses are minimised. Oxidation is complete for all (relevant) organic components after approx. 1 minute. This assessment is evident from FIG. 3, which plots conductivity differences D against TOC concentration (in ppb) for three oxidation times (1 minute, 3 minutes and 6 minutes). The varying conductivity differences D at longer oxidation times (3 and 6 minutes, compared to 1 minute) are caused for the greater part by the resulting higher temperature of the water or liquid.

The control/analysis unit 6 does not simply determine the maximum value M according to FIG. 2, and the attendant difference D=M−G. This equipment also allows control over the rate of flow through the measuring cell 3 by altering the cross-sectional area of the choke valve 11. In effect, this means that the relationship between the flow through the reaction chamber 1 and the measuring cell 3 and that through the bypass 12 can be set. In this way, the time axis of FIG. 2 can be varied as it were, since the speed of the "sample column", corresponding to the sample quantity, can be varied. It follows that the peak illustrated in FIG. 2 can be more or less "pulled apart" in time, according to how high the flow speed and the dependent rate of flow is. In any case this method allows an unambiguous determination of the maximum M—even when very little carbon content (TOC) is present.

The procedure illustrated in FIG. 2 results from an approximately 3 minute long flushing period, then an approximately 1,5 minute long oxidation period followed by values being taken. Afterwards, another 3 minute long flush followed.

What is claimed is:

1. A method for the determination of the total organic carbon (TOC) content of liquids, including ultra-pure water, said method comprising:

locating a liquid sample containing organic carbon in a reaction chamber;

treating the sample statically, batch by batch, using UV radiation to oxidize the carbon mainly to carbon dioxide, wherein the sample is irradiated by a UV immersion lamp submerged in the sample until the organic carbon contained in the sample is completely oxidized;

transferring the sample to a measuring cell connected to the reaction chamber by liquid entering the reaction chamber from outside the reaction chamber;

measuring the conductivity of the sample in the measuring cell; and determining the carbon content (TOC) in the sample based on the conductivity measurement, wherein:

the carbon dioxide concentration which is proportional to the carbon content of the sample is dynamically registered as the sample flows through the measuring cell, wherein a base value (G) of the carbon dioxide concentration corresponding to untreated liquid and a maximum value (M) of the enriched carbon dioxide concentration appearing after carbon oxidation in the course of the liquid enriched with carbon dioxide flowing through the measuring cell, are measured and wherein the difference (D), which is dependent upon the carbon content of the liquid, between the maximum value (M) and the base value (G) is found (D=M−G).

2. The method in accordance with claim 1, wherein the liquid under investigation is used as liquid entering the reaction chamber from outside the reaction chamber after oxidation of the carbon.

3. The method in accordance with claim 1, wherein before and/or after the determination of carbon dioxide concentration, the reaction chamber and the measuring cell are cleaned by means of liquid flowing through the reaction chamber and the measuring cell, respectively.

4. A method for the determination of the total organic carbon (TOC) content of liquids, including ultra-pure water, said method comprising:

locating a liquid sample containing organic carbon in a reaction chamber;

irradiating the sample statically batch by batch using UV radiation to oxidize the carbon in the sample mainly to carbon dioxide, wherein the sample is irradiated by a UV immersion lamp submerged in the sample until the organic carbon contained in the sample is completely oxidized;

transferring the sample quantity to a measuring cell connected to the reaction chamber by liquid entering the reaction chamber from outside the reaction chamber;

measuring the conductivity of the sample in the measuring chamber;

determining the carbon content (TOC) in the sample from the conductivity measurement, wherein:

the carbon dioxide concentration which is proportional to the carbon content of the liquid is dynamically registered as the sample flows through the measuring cell, wherein a base value (G) of the carbon dioxide concentration corresponding to the untreated liquid is measured, and the integral of the signal reduced by the base value (G) is calculated as area (F), wherein the area (F) represents the carbon content.

5. The method in accordance with claim 4, wherein the liquid under investigation is used as liquid entering the reaction chamber from outside the,reaction chamber after oxidation of the carbon.

6. The method in accordance with claim 4, wherein before and/or after the determination of carbon dioxide concentration, the reaction chamber and the measuring cell are cleaned by means of liquid flowing through the reaction chamber and the measuring cell, respectively.

7. An apparatus for the determination of the total organic carbon (TOC) content of liquids, including ultra-pure water, said apparatus comprising:

a reaction chamber with an inlet and an outlet for accommodation of a sample quantity of the liquid having dissolved carbon;

a UV immersion lamp mounted in the reaction chamber and submergable in the liquid in the reaction chamber for treating the sample quantity with UV radiation statically for oxidation of the dissolved carbon in the sample quantity of the liquid;

a cut-off device which can be closed for stopping the flow of the liquid after introduction of the sample quantity into the reaction chambers and which can be opened after oxidation of the carbon dissolved in the sample quantity to carbon dioxide,; and a measuring cell with an inlet connected to the outlet of the reaction chamber and an outlet connected to the cut-off device and further with a carbon dioxide concentration sensor for dynamically registering the carbon dioxide concentration of the liquid, which is proportional to the carbon content, as the liquid flows through the measuring cell from its inlet to its outlet after opening of the cut-off device;

wherein from signals of the carbon dioxide concentration sensor with the aid of a control/analysis unit a base value (G) of a carbon dioxide concentration corresponding to untreated liquid, by differentiation over time a maximum value (M), of carbon dioxide concentration after carbon oxidation, the difference (D=M−G) between both values, or the integral (F) of the signals reduced by the base value (G) are determinable, wherein the difference (D) and the integral (F) correspond to the carbon content of the liquid.

8. The apparatus in accordance with claim 7, wherein the cut-off device has the form of an electro-magnetically controlled valve.

9. The apparatus in accordance with claim 8, wherein the electro-magnetically controlled valve is connected to a control/analysis unit.

10. The apparatus in accordance with claim 8, wherein the measuring cell comprises one or more conductivity sensors.

11. The apparatus in accordance with claim 7, wherein the measuring cell comprises one or more conductivity sensors.

12. The apparatus in accordance with claim 11, wherein one or more of the conductivity sensors are connected to a control/analysis unit.

13. The apparatus in accordance with claim 7, wherein the measuring cell is formed rotationally symmetrically and the measuring cell further comprises an inlet and an outlet, the inlet and outlet each have the same cross-section.

14. The apparatus in accordance with claim 7, wherein the UV immersion lamp is mounted in the middle of the reaction chamber on an axis of symmetry S, wherein the reaction chamber and the UV immersion lamp are rotationally symmetrically formed with regard to the axis of symmetry (S).

15. The apparatus in accordance with claim 7, wherein the reaction chamber and the UV immersion lamp form a compact assembly unit.

16. The apparatus in accordance with claim 7, wherein the reaction chamber has the form of a rotating U-pipe.

17. The apparatus of claim 16, wherein the U-pipe has a cross-sectional dimension in the range of 1 to 5 mm.

18. The apparatus in accordance with claim 7, wherein an adjustable choke valve is fitted between the reaction chamber and the measuring cell to control the rate of flow through the measuring cell.

19. The apparatus in accordance with claim 7, wherein a bypass with an electro-magnetically controlled valve is fitted parallel to the reaction chamber and the measuring cell.

20. The apparatus in accordance with claim 7, wherein the cut-off device has the form of an electro-magnetically controlled valve;

an adjustable choke valve is fitted between the reaction chamber and the measuring cell to control the rate of flow through the measuring cell;

a bypass with an electro-magnetically controlled valve is fitted parallel to the reaction chamber and the measuring cell; and the measuring cell for determination of the carbon dioxide concentration of the liquid comprises one or more conductivity sensors, wherein all of the valves, together with the conductivity sensor or sensors, are connected to a control/analysis unit.

21. An apparatus for the determination of the total organic carbon (TOC) content of liquids, including ultra-pure water, said apparatus comprising:
- a reaction chamber with an inlet for accommodation of a sample quantity of the liquid having dissolved carbon and for accommodation of static oxidation of the dissolved carbon;
- a measuring cell connected to the reaction chamber into which the sample quantity can be transferred, after oxidation of the carbon, by liquid entering the reaction chamber from outside the reaction chamber, the measuring cell comprising one or more conductivity sensors;
- a UV immersion lamp mounted in the reaction chamber and submergable in the liquid in the reaction chamber; and
- a cut-off device disposed on an outlet side of the measuring cell, which can be closed after introduction of the sample quantity into the reaction chamber and, after static oxidation of the carbon dissolved in the sample quantity to carbon dioxide, the cut-off device can be opened;
- wherein a carbon dioxide concentration which is proportional to the carbon content of the liquid can be dynamically registered as the liquid flows through the measuring cell; and
- wherein with the aid of a control/analysis unit, a base value (G) of a carbon dioxide concentration corresponding to untreated liquid, a carbon dioxide concentration after carbon oxidation by differentiation over time a maximum value (M), and a carbon dioxide concentration related to the difference (D=M−G) or by integration of a signal reduced by the base value (G), the area (F) can be found.

22. The apparatus in accordance with claim 21, wherein the cut-off device has the form of an electro-magnetically controlled valve.

23. The apparatus in accordance with claim 21, wherein the measuring cell is formed rotationally symmetrically and the measuring cell further comprises an inlet and an outlet, the inlet and outlet each have the same cross-section.

24. The apparatus in accordance with claim 21, wherein the UV immersion lamp is mounted in the middle of the reacting chamber on an axis of symmetry S, wherein the reaction chamber and the UV immersion lamp are rotationally symmetrically formed with regard to the axis of symmetry (S).

25. The apparatus in accordance with claim 21, wherein the reaction chamber and the UV immersion lamp form a compact assembly unit.

26. The apparatus in accordance with claim 21, wherein the reaction chamber has the form of a rotating U-pipe.

27. The apparatus of claim 26, wherein the U-pipe has a cross-sectional dimension in the range of 1 to 5 mm.

28. The apparatus in accordance with claim 21, wherein an adjustable choke valve is fitted between the reaction chamber and the measuring cell to control the rate of flow through the measuring cell.

29. The apparatus in accordance with claim 21, wherein a bypass with an electro-magnetically controlled valve is fitted parallel to the reaction chamber and the measuring cell.

30. The apparatus in accordance with claim 21, wherein one or more of the conductivity sensors are connected to a control/analysis unit.

31. The apparatus in accordance with claim 21, wherein the electro-magnetically controlled valve is connected to a control/analysis unit.

* * * * *